US011761104B2

(12) United States Patent
Chishima

(10) Patent No.: US 11,761,104 B2
(45) **Date of Patent: *Sep. 19, 2023**

(54) FUEL PRODUCTION SYSTEM

(71) Applicant: Honda Motor Co., Ltd., Tokyo (JP)

(72) Inventor: Hiroshi Chishima, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/831,667

(22) Filed: Jun. 3, 2022

(65) Prior Publication Data

US 2022/0403536 A1 Dec. 22, 2022

(30) Foreign Application Priority Data

Jun. 7, 2021 (JP) ................................ 2021-094873

(51) Int. Cl.

| | |
|---|---|
| ***C25B 15/08*** | (2006.01) |
| ***C25B 1/04*** | (2021.01) |
| ***C25B 15/023*** | (2021.01) |
| ***C10J 3/72*** | (2006.01) |
| ***C07C 29/152*** | (2006.01) |

(52) U.S. Cl.

CPC .......... *C25B 15/081* (2021.01); *C07C 29/152* (2013.01); *C10J 3/723* (2013.01); *C25B 1/04* (2013.01); *C25B 15/023* (2021.01); *C10J 2300/0916* (2013.01); *C10J 2300/0966* (2013.01); *C10J 2300/1284* (2013.01); *C10J 2300/1665* (2013.01)

(58) Field of Classification Search

CPC ....... C25B 15/081; C25B 1/04; C25B 15/023; C10J 2300/0916; C10J 2300/0966; C10J 2300/1284; C10J 2300/1665; C07C 29/152

See application file for complete search history.

(56) References Cited

FOREIGN PATENT DOCUMENTS

JP 2002193858 A 7/2002

*Primary Examiner* — Jafar F Parsa
(74) *Attorney, Agent, or Firm* — Duft & Bornsen, PC

(57) ABSTRACT

Fuel production system includes: synthesis gas generation unit configured to generate synthesis gas containing hydrogen and carbon monoxide from carbon-containing raw material; fuel production unit configured to produce fuel from synthesis gas generated; water electrolyzer configured to electrolyze water to generate water-electrolyzed hydrogen; hydrogen supply unit configured to supply water-electrolyzed hydrogen generated to synthesis gas generation unit; and controller. The controller is configured to perform: calculating input energy based on first energy possessed by raw material, second energy consumed by water electrolyzer, third energy consumed by synthesis gas generation unit, and fourth energy consumed by fuel production unit; calculating recovered energy based on fifth energy possessed by fuel produced; and determining supply amount of water-electrolyzed hydrogen to be supplied based on input energy and recovered energy calculated.

5 Claims, 4 Drawing Sheets

FUEL PRODUCTION SYSTEM

CROSS-REFERENCE TO RELATED APPLICATION

This application is based upon and claims the benefit of priority from Japanese Patent Application No. 2021-094873 filed on Jun. 7, 2021, the content of which is incorporated herein by reference.

BACKGROUND OF THE INVENTION

Field of the Invention

This invention relates to a fuel production system configured to produce fuel by electrolyzing water.

Description of the Related Art

Conventionally, as this type of apparatus, apparatuses are known that produce methanol using biomass as raw material (for example, Japanese Unexamined Patent Publication No. 2002-193858 (JP2002-193858A)). The apparatus described in JP2002-193858A electrolyzes water to generate hydrogen by solar power and wind power, and replenishes this hydrogen into a gas containing carbon monoxide and hydrogen obtained by gasifying biomass, whereby adjusting the ratio of the carbon monoxide and the hydrogen to a ratio suitable for methanol synthesis.

However, as the apparatus described in JP2002-193858A, when producing fuel by utilizing renewable power such as solar power or wind power, although carbon emissions can be reduced, there is a risk of increasing energy loss and fuel production costs.

SUMMARY OF THE INVENTION

An aspect of the present invention is a fuel production system, including: a synthesis gas generation unit configured to generate synthesis gas containing hydrogen and carbon monoxide from carbon-containing raw material; a fuel production unit configured to produce fuel from the synthesis gas generated by the synthesis gas generation unit; a water electrolyzer configured to electrolyze water to generate water-electrolyzed hydrogen; a hydrogen supply unit configured to supply the water-electrolyzed hydrogen generated by the water electrolyzer to the synthesis gas generation unit; and a controller including an arithmetic unit and a storage unit. The controller is configured to perform: calculating an input energy based on a first energy possessed by the carbon-containing raw material, a second energy consumed by the water electrolyzer when generating the water-electrolyzed hydrogen, a third energy consumed by the synthesis gas generation unit when generating the synthesis gas, and a fourth energy consumed by the fuel production unit when producing the fuel; calculating a recovered energy based on a fifth energy possessed by the fuel produced by the fuel production unit; and determining a supply amount of the water-electrolyzed hydrogen to be supplied by the hydrogen supply unit based on the input energy and the recovered energy calculated.

BRIEF DESCRIPTION OF THE DRAWINGS

The objects, features, and advantages of the present invention will become clearer from the following description of embodiments in relation to the attached drawings, in which.

DETAILED DESCRIPTION OF THE INVENTION

An embodiment of the present invention is explained with reference to FIGS. 1 to 6B in the following. A fuel production system according to the embodiment of the present invention electrolyzes water by renewable power such as solar power or wind power to generate hydrogen (water-electrolyzed hydrogen), and uses this water-electrolyzed hydrogen to produce so-called electrosynthetic fuel (e-fuel) from carbon-containing raw materials such as biomass. In the following, an example will be explained in particular in which biomass is gasified to generate a synthesis gas containing hydrogen and carbon monoxide, and a methanol fuel is produced from the generated synthesis gas.

Figure 1:
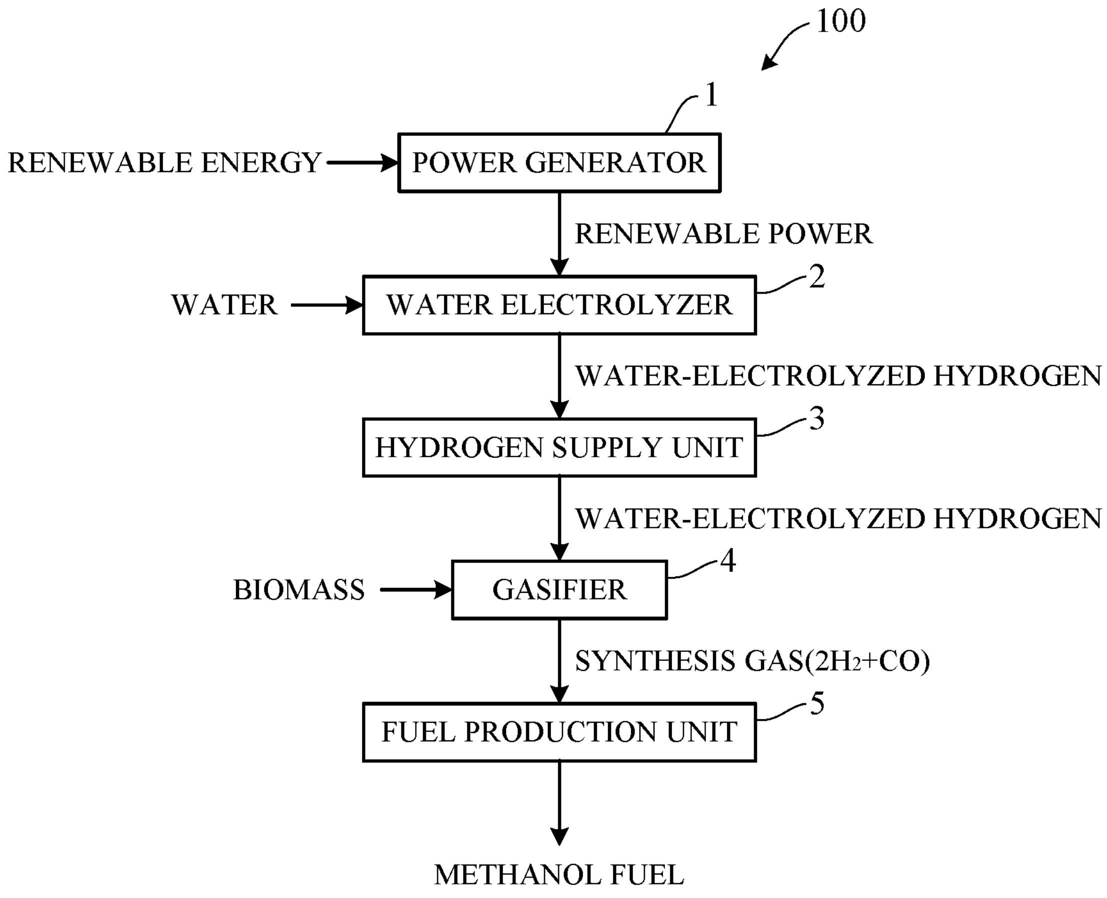
FIG. 1 is a block diagram schematically showing an example of overall configuration of a fuel production system according to an embodiment of the present invention.

FIG. 1 is a block diagram schematically showing an example of overall configuration of a fuel production system 100 according to the embodiment of the present invention. As shown in FIG. 1, the fuel production system 100 includes a power generator 1, a water electrolyzer 2, a hydrogen supply unit 3, a gasifier 4, and a fuel production unit 5.

The power generator 1 is configured, for example, as a solar power generator that converts solar energy into electrical energy using semiconductor devices or a wind power generator that converts wind energy into electrical energy using a windmill, and generates renewable power. The renewable power generated by the power generator 1 is supplied to the water electrolyzer 2, the hydrogen supply unit 3, the gasifier 4, and the fuel production unit 5.

The water electrolyzer 2 generates water-electrolyzed hydrogen by electrolyzing water using the renewable power generated by the power generator 1. The water electrolyzer 2 is provided with sensors that measure an electrolysis voltage of the water electrolyzer 2, a power consumption of the water electrolyzer 2, a generation amount (for example, mass flow rate) m of the water-electrolyzed hydrogen, and the like.

The hydrogen supply unit 3 is configured, for example, as a part of the water electrolyzer 2, and supplies all of the water-electrolyzed hydrogen generated by the water electrolyzer 2 to the gasifier 4. The hydrogen supply unit 3 includes, for example, a flow control valve that controls or regulates a water flow rate supplied to the water electrolyzer 2 by adjusting the water supply amount, and adjusts the generation amount of the water-electrolyzed hydrogen by the water electrolyzer 2 to adjust the supply amount of the water-electrolyzed hydrogen to the gasifier 4. The hydrogen supply unit 3 may be provided separately from the water electrolyzer 2. For example, the hydrogen supply unit 3 may be configured as a hydrogen tank that stores the water-electrolyzed hydrogen generated by the water electrolyzer 2 and a flow control valve that controls or regulates the flow rate of the water-electrolyzed hydrogen supplied from the hydrogen tank to the gasifier 4.

The gasifier 4 mainly includes a gasification furnace, and performs gasification by heating the gasification furnace using the renewable power generated by the power generator 1 to generate the synthesis gas. Biomass such as rice husk, bagasse, or wood subjected to pretreatment such as drying and grinding, oxygen, and water (steam) are supplied to the gasification furnace of the gasifier 4, and the synthesis gas containing hydrogen and carbon monoxide is generated through reactions of the following formulas (i) to (v). The reactions of the formulas (ii) to (v) are equilibrium reactions.

$$C+O_2 \rightarrow CO_2 \quad (i)$$

$$C+H_2O \rightarrow CO+H_2 \quad (ii)$$

$$C+2H_2 \rightarrow CH_4 \quad (iii)$$

$$C+CO_2 \rightarrow 2CO \quad (iv)$$

$$CO+H_2O \rightarrow CO_2+H_2 \quad (v)$$

Further, all of the water-electrolyzed hydrogen generated by the water electrolyzer 2 is supplied to the gasification furnace of the gasifier 4 through the hydrogen supply unit 3. The gasifier 4 is provided with sensors that measure a power consumption of the gasifier 4, a temperature and a pressure of the synthesis gas in the gasification furnace, a generation amount (for example, mass flow rate) of the synthesis gas, a partial pressure (concentration) of each gas component, and the like. The supply amount of biomass, oxygen, water, and water-electrolyzed hydrogen to the gasification furnace is controlled on the basis of measured values of these sensors.

By supplying the water-electrolyzed hydrogen from the hydrogen supply unit 3, the equilibrium reaction (shift reaction) of the formula (v) shifts in a direction that promotes the production of carbon monoxide and suppresses the production of carbon dioxide. Further, by controlling the supply amount m of the water-electrolyzed hydrogen generated by the water electrolyzer 2 and supplied by the hydrogen supply unit 3, the composition of the synthesis gas is adjusted to a composition suitable for the subsequent fuel production. For example, when producing the methanol fuel in the subsequent fuel production unit 5, the composition is adjusted so that the ratio (partial pressure ratio) of hydrogen to carbon monoxide in the synthesis gas becomes "2" in accordance with the methanol synthesis reaction of the following formula (vi).

$$CO+2H_2 \rightarrow CH_3OH \quad (vi)$$

The fuel production unit 5 mainly includes a reactor and a distillation column. The synthesis gas generated by the gasifier 4 and subjected to posttreatment such as ash removal and desulfurization by washing is supplied to the reactor of the fuel production unit 5, and the methanol fuel is generated by the exothermic reaction of the formula (vi). More specifically, the product gas is distilled by heating the distillation column using the renewable power generated by the power generator 1, and the methanol fuel is obtained. The reactor and the distillation column of the fuel production unit 5 are respectively provided with sensors that measure a temperature and a pressure, a generation amount (for example, mass flow rate) and a concentration of the methanol fuel, and the like.

The fuel production system 100 further includes a compressor between the gasifier 4 and the fuel production unit 5, and the synthesis gas is delivered from the gasifier 4 to the fuel production unit 5 using the renewable power generated by the power generator 1. The fuel production system 100 further includes a sensor for measuring a power consumption of the compressor.

As described above, the fuel production system 100 can reduce emission of carbon dioxide as a whole by using the renewable energy. However, if the energy loss becomes large in the process of conversion of renewable energy, the energy loss and the fuel production cost of the whole system may increase. Therefore, the fuel production system 100 according to the embodiment of the present invention is configured as set out in the following so as to suppress the energy loss and the fuel production cost while suppressing emission of carbon dioxide in the fuel production by paying attention to the energy balance of the whole system.

Figure 2:
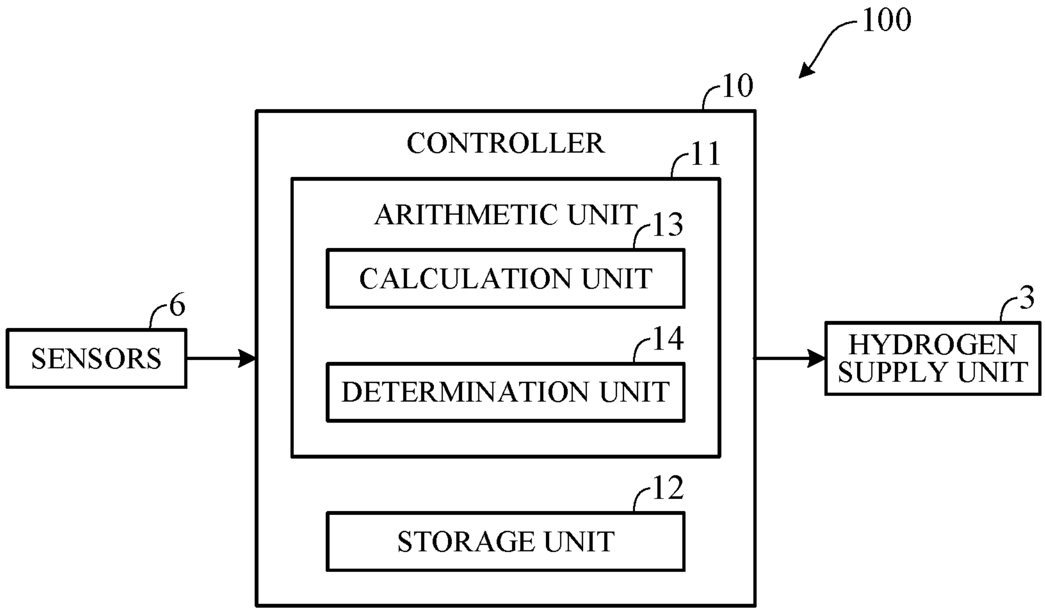
FIG. 2 is a block diagram schematically showing an example of main configuration of the fuel production system according to the embodiment of the present invention.

FIG. 2 is a block diagram schematically showing an example of main configuration of the fuel production system 100 according to the embodiment of the present invention. As shown in FIG. 2, the fuel production system 100 includes a controller 10. The controller 10 is connected with sensors 6 including the sensors described above, and the hydrogen supply unit 3. The controller 10 controls operation of the hydrogen supply unit 3 by performing predetermined processing on the basis of signals from the sensors 6.

The controller 10 includes a computer including an arithmetic unit 11 such as CPU, a storage unit 12 such as ROM or RAM, and other peripheral circuits such as I/O interface (not shown). The storage unit 12 stores information such as various control programs and threshold values used in the programs. The arithmetic unit 11 includes, as a functional configuration, a calculation unit 13, and a determination unit 14. In other words, the arithmetic unit 11 such as the CPU of the controller 10 functions as the calculation unit 13 and the determination unit 14.

Figure 3:
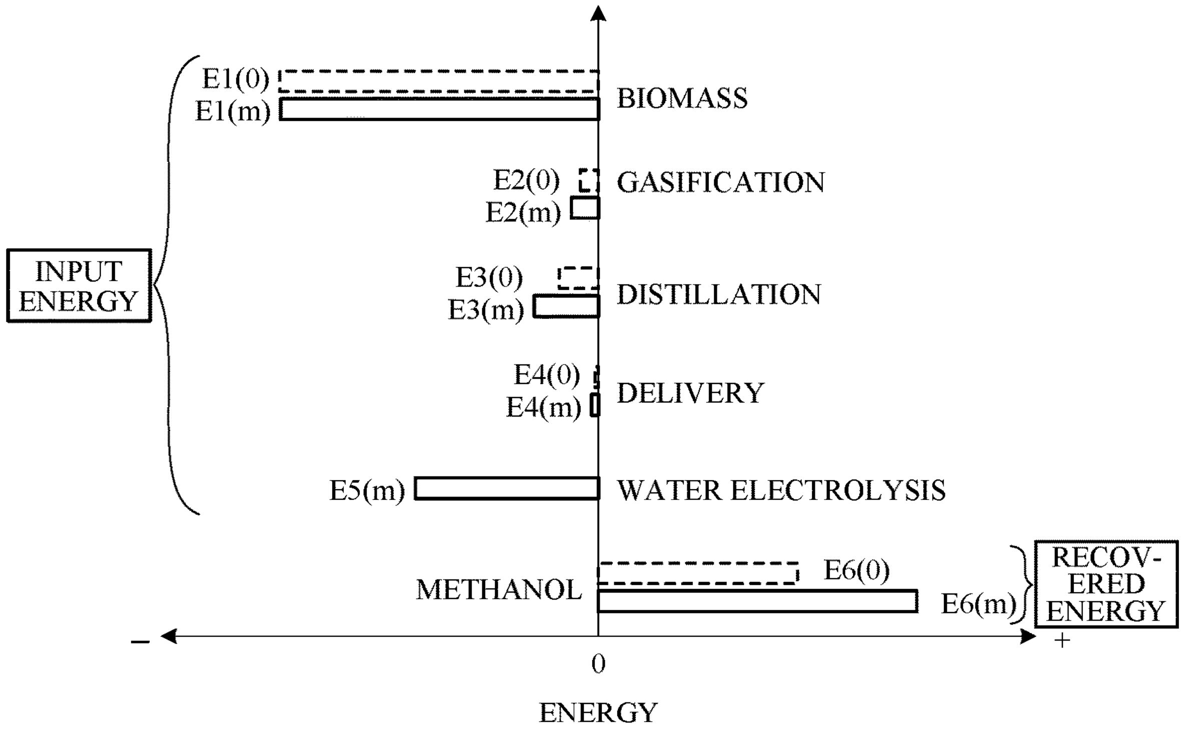
FIG. 3 is a diagram for explaining an energy balance of the fuel production system of FIG. 1.

FIG. 3 is a diagram for explaining the energy balance of the fuel production system 100, showing an example of input energy and recovered energy per unit amount of the raw material in the production of the methanol fuel using biomass as the raw material. The input energy includes an energy (calorific value) E1 possessed by a unit amount of biomass, energies E2 to E5 respectively required for gasification of the raw material (heating of the gasification furnace), distillation of the fuel, delivery of the synthesis gas, and electrolysis of water. The recovered energy includes an energy (calorific value) E6 possessed by the methanol fuel produced from a unit amount of biomass.

In FIG. 3, an energy E(0) for a case where the water-electrolyzed hydrogen is not supplied by the hydrogen supply unit 3 is shown as a broken line, and an energy E(m) for a case where the water-electrolyzed hydrogen is supplied is shown as a solid line, respectively. As shown in FIG. 3, in the case where the water-electrolyzed hydrogen is supplied by the hydrogen supply unit 3, the energy E5(m) required for electrolysis is input depending on the supply amount of the water-electrolyzed hydrogen and the energies E2(m) to E4(m) respectively required for gasification, distillation and delivery increase, while the energy E6(m) recovered as the methanol fuel increases.

The calculation unit 13 calculates the sum of energies E1(0) to E4(0) for the case where the water-electrolyzed hydrogen is not supplied as a standard input energy Ein(0), and calculates the sum of energies E1(m) to E5(m) for the case where the water-electrolyzed hydrogen is supplied as an input energy Ein(m), respectively, as the following formulas (vii) and (viii). The calculation unit 13 also calculates the energy E6(0) for the case where the water-electrolyzed hydrogen is not supplied by the hydrogen supply unit 3 as a standard recovered energy Eout(0), and calculates the energy E6(m) for the case where the water-electrolyzed hydrogen is supplied by the hydrogen supply unit 3 as a recovered energy Eout(m), respectively, as the following formulas (ix) and (x).

$$Ein(0)=E1(0)+E2(0)+E3(0)+E4(0) \quad \text{(vii)}$$

$$Ein(m)=E1(m)+E2(m)+E3(m)+E4(m)+E5(m) \quad \text{(viii)}$$

$$Eout(0)=E6(0) \quad \text{(ix)}$$

$$Eout(m)=E6(m) \quad \text{(x)}$$

The energy E2 required for gasification of the raw material is calculated based on the standard reaction enthalpy and the amount of synthesis gas generated from the unit amount of biomass. The energy E2 can also be calculated based on the power consumption of the gasifier 4. The energy E3 required for distillation of the fuel is calculated based on the production amount and the concentration of the methanol fuel produced from the unit amount of biomass. The energy E3 can also be calculated based on the power consumption of the fuel production unit 5. The energy E4 required for delivery of the synthesis gas is calculated based on a compression work per unit amount and the amount of the synthesis gas generated from the unit amount of biomass. The energy E4 can also be calculated based on the power consumption of the compressor.

The energy E5 required for electrolysis of water is calculated based on the standard reaction enthalpy and the amount of the water-electrolyzed hydrogen generated from the unit amount of biomass and an electrolysis efficiency p of the water electrolyzer 2, as the following formula (xi). The electrolysis efficiency of the water electrolyzer 2 is calculated based on the electrolysis voltage for the case where the electrolysis efficiency is 100% (for example, 1.48[V]) and the electrolysis voltage of the water electrolyzer 2, as the following formula (xii). The energy E5 required for electrolysis of water can also be calculated based on the power consumption of the water electrolyzer 2. It should be noted that, when water is electrolyzed using renewable power such as solar power or wind power, the power may be insufficient depending on weather conditions and the like, and the water electrolyzer 2 may not be able to operate at the rated capacity. In such case, the electrolysis efficiency p of the water electrolyzer 2 decreases.

$$E5=(\text{standard reaction enthalpy})\times(\text{amount of generated water-electrolyzed hydrogen})/p \quad \text{(xi)}$$

$$p=1.48/(\text{electrolysis voltage}) \quad \text{(xii)}$$

The calculation unit 13 calculates a difference ΔEin(m) between the standard input energy Ein(0) and the input energy Ein(m), and calculates a difference ΔEout(m) between the standard recovered energy Eout(0) and the recovered energy Eout(m), as the following formulas (xiii) and (xiv). The calculation unit 13 also calculates an energy conversion efficiency of the fuel production system 100, as the following formula (xv). The calculation unit 13 further calculates an evaluation value of the energy balance, as the following formula (xvi).

$$\Delta Ein(m) = Ein(m) - Ein(0) \quad \text{(xiii)}$$

$$\Delta Eout(m) = Eout(m) - Eout(0) \quad \text{(xiv)}$$

$$(\text{energy conversion efficiency}) = Eout/Ein = E6/(E1+E2+E3+E4+E5) \quad \text{(xv)}$$

$$(\text{evaluation value of energy balance}) = \Delta Eout(m)/\Delta Ein(m) \quad \text{(xvi)}$$

Figure 4:
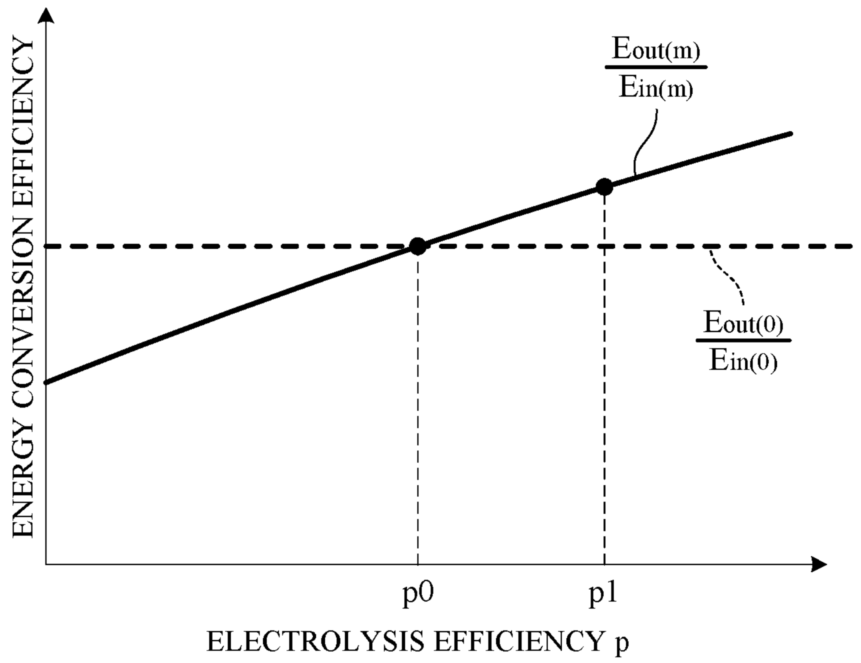
FIG. 4 is a diagram for explaining relationship between an electrolysis efficiency of a water electrolyzer of FIG. 1 and an energy conversion efficiency of the fuel production system.

FIG. 4 is a diagram for explaining relationship between the electrolysis efficiency p of the water electrolyzer 2 and the energy conversion efficiency of the fuel production system 100. In FIG. 4, the energy conversion efficiency Eout(0)/Ein(0) for the case where the water-electrolyzed hydrogen is not supplied by the hydrogen supply unit 3 is shown as a broken line, and the energy conversion efficiency Eout(m)/Ein(m) for the case where the water-electrolyzed hydrogen is supplied by the hydrogen supply unit 3 is shown as a solid line, respectively. As shown in FIG. 4, the energy conversion efficiency Eout(m)/Ein(m) of the fuel production system 100 for the case where the water-electrolyzed hydrogen is supplied increases as the electrolysis efficiency p of the water electrolyzer 2 increases. For this reason, under an operation condition of a predetermined electrolysis efficiency p0 or higher, the energy conversion efficiency increases by supplying the water-electrolyzed hydrogen as compared with the case where the water-electrolyzed hydrogen is not supplied. On the other hand, under an operation condition of the predetermined electrolysis efficiency p0 or lower, the energy conversion efficiency decreases by supplying the water-electrolyzed hydrogen as compared with the case where the water-electrolyzed hydrogen is not supplied.

Figure 5:
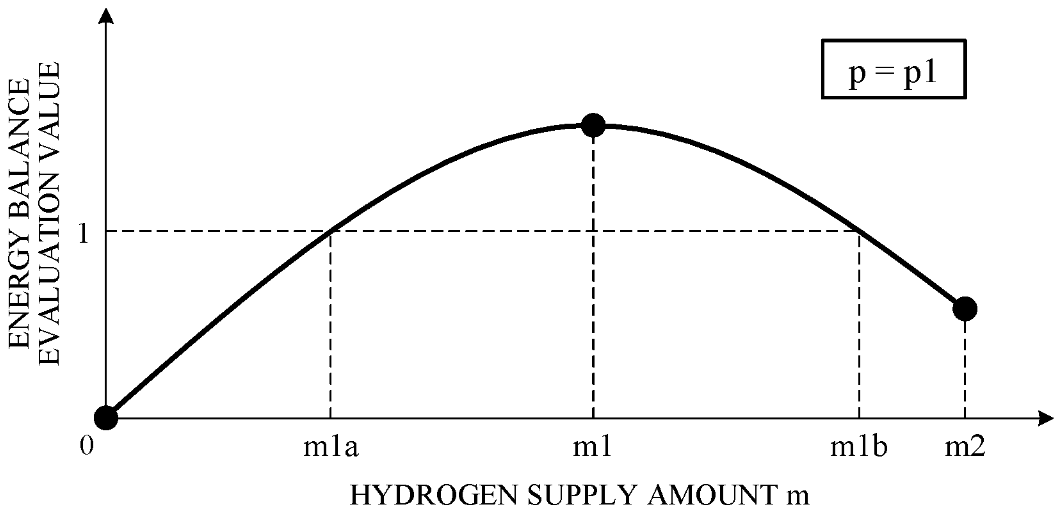
FIG. 5 is a diagram for explaining relationship between a hydrogen supply amount by a hydrogen supply unit of FIG. 1 and an evaluation value of the energy balance of the fuel production system.

FIG. 5 is a diagram for explaining relationship between the supply amount m of the water-electrolyzed hydrogen supplied by the hydrogen supply unit 3 and the evaluation value of the energy balance of the fuel production system 100. FIG. 5 shows an example of the evaluation value when changing the supply amount m of the water-electrolyzed hydrogen under an operation condition corresponding to the electrolysis efficiency p1 of FIG. 4. As shown in FIG. 5, the supply amount m of the water-electrolyzed hydrogen has an optimal quantity m1 depending on operation conditions such as the electrolysis efficiency p and the like. When controlling the supply amount m of the water-electrolyzed hydrogen within an appropriate range m1*a* to m1*b* where the evaluation value of the energy balance is "1" or higher, the energy conversion efficiency increases as compared with the case where the water-electrolyzed hydrogen is not supplied. On the other hand, when supplying the water-electrolyzed hydrogen of an excess amount m2 exceeding the appropriate range m1*a* to m1*b* (for example, "1.5" times the optimal quantity m1), the evaluation value of the energy balance decreases below "1" and the energy conversion efficiency decreases as compared with the case where the water-electrolyzed hydrogen is not supplied.

Figure 6A:
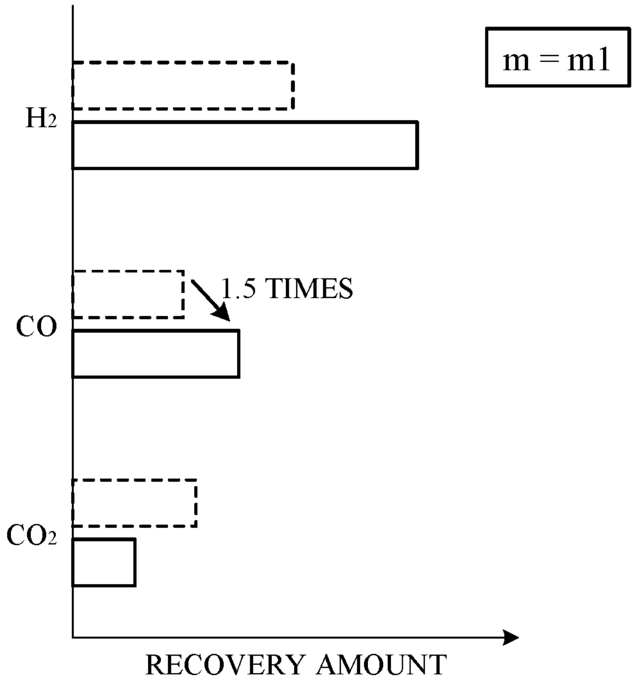
FIG. 6A is a diagram showing an example of a recovery amount of each gas component from a gasifier of FIG. 1.
Figure 6B:
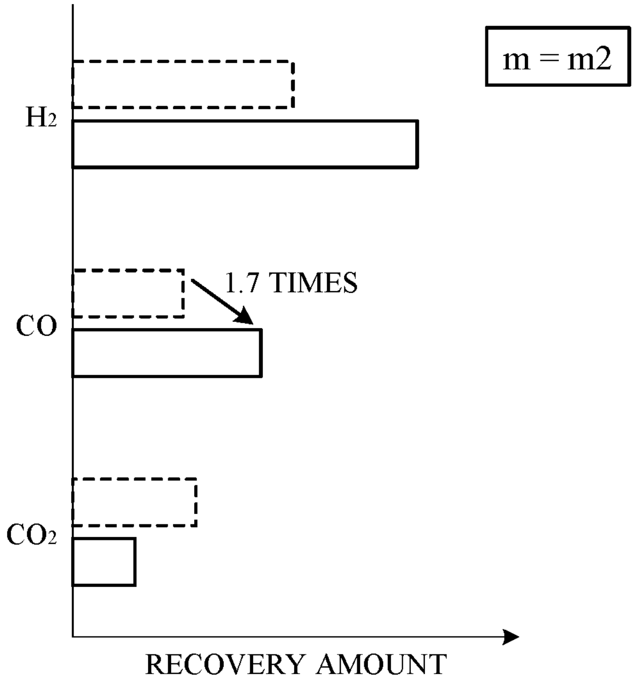
FIG. 6B is a diagram showing another example of the recovery amount of each gas component from the gasifier of FIG. 1.

FIGS. 6A and 6B are diagrams showing an example of the recovery amount (for example, mass flow rate) of each gas component from the gasifier 4. In FIGS. 6A and 6B, the recovery amount for the case where the water-electrolyzed hydrogen is not supplied by the hydrogen supply unit 3 is shown as a broken line, and the recovery amount for the case where the water-electrolyzed hydrogen is supplied by the hydrogen supply unit 3 is shown as a solid line, respectively. FIG. 6A shows an example of the recovery amount of each gas component for a case where the supply amount m of the water-electrolyzed hydrogen in FIG. 5 is the optimal quantity m1, and FIG. 6B shows an example of the recovery amount of each gas component for a case where the supply amount m of the water-electrolyzed hydrogen is the excess amount m2.

In the example shown in FIG. 6A, the supply amount m of the water-electrolyzed hydrogen has been adjusted to the optimal quantity m1, and the recovery amount of carbon monoxide corresponding to the production amount of the methanol fuel has increased by "1.5" times that for the case where the water-electrolyzed hydrogen is not supplied. On the other hand, in the example shown in FIG. 6B, the supply amount m of the water-electrolyzed hydrogen has been adjusted to the excess amount m2, which is "1.5" times the optimal quantity m1, and the recovery amount of carbon monoxide has increased by "1.7" times that for the case where the water-electrolyzed hydrogen is not supplied. Comparing the example of FIG. 6A with the example of FIG. 6B, the supply amount m of the water-electrolyzed hydrogen corresponding to the input energy increases by "1.5" times, whereas the recovery amount of carbon monoxide corresponding to the recovered energy increases only by a factor of about "1.1" times. As described above, if the supply amount m of the water-electrolyzed hydrogen increases beyond the appropriate range, the energy conversion efficiency decreases more than in the case where the water-electrolyzed hydrogen is not supplied.

The determination unit 14 determines the supply amount m of the water-electrolyzed hydrogen supplied by the hydrogen supply unit 3 based on the evaluation value of the energy balance ΔEout(m)/ΔEin(m) calculated by the calculation unit 13. Specifically, the determination unit 14 determines the supply amount m of the water-electrolyzed hydrogen so that the evaluation value of the energy balance ΔEout(m)/ΔEin(m) becomes "1" or higher. With this, it becomes possible to operate the fuel production system 100 in an operation range where the energy conversion efficiency increases by supplying the water-electrolyzed hydrogen.

The present embodiment can achieve advantages and effects such as the following:

(1) The fuel production system 100 includes: the gasifier 4 configured to generate the synthesis gas containing hydrogen and carbon monoxide from biomass; the fuel production unit 5 configured to produce the methanol fuel from the synthesis gas generated by the gasifier 4; the water electrolyzer 2 configured to electrolyze water to generate water-electrolyzed hydrogen; the hydrogen supply unit 3 configured to supply the water-electrolyzed hydrogen generated by the water electrolyzer 2 to the gasifier 4; the calculation unit 13 configured to calculate the input energy Ein(m) based on the energy E1 possessed by the biomass, the energy E5 consumed by the water electrolyzer 2 when generating the water-electrolyzed hydrogen, the energy E2 consumed by the gasifier 4 when generating the synthesis gas, and the energy E3 consumed by the fuel production unit 5 when producing the methanol fuel, and configured to calculate the recovered energy Eout(m) based on the energy E6 possessed by the methanol fuel produced by the fuel production unit 5; and the determination unit 14 configured to determine the supply amount in of the water-electrolyzed hydrogen to be supplied by the hydrogen supply unit 3 based on the input energy Ein(m) and the recovered energy Eout(m) calculated by the calculation unit 13 (FIGS. 1 to 3).

By monitoring the energy conversion efficiency of the fuel production system 100 as a whole through the input energy Ein(m) and the recovered energy Eout(m) and determining the supply amount m of the water-electrolyzed hydrogen, it becomes possible to suppress the energy loss in the fuel production. Specifically, although the energy loss in the energy conversion process increases depending on weather conditions and the like when using renewable power, the energy loss can be suppressed by determining the supply amount m of the water-electrolyzed hydrogen so that the energy conversion efficiency increases as compared with the case where the water-electrolyzed hydrogen is not supplied.

(2) The calculation unit 13 calculates the energy E5 consumed by the water electrolyzer 2 when generating the water-electrolyzed hydrogen based on the generation amount of the water-electrolyzed hydrogen generated by the water electrolyzer 2 and the electrolysis efficiency of the water electrolyzer 2. With this, it becomes possible to calculate the electrolysis efficiency p based on the actually measured electrolysis voltage to calculate the energy E5 consumed by the water electrolyzer 2 when generating the water-electrolyzed hydrogen.

(3) The calculation unit 13 calculates the energy E5 consumed by the water electrolyzer 2 when generating the water-electrolyzed hydrogen based on the power consumption consumed by the water electrolyzer 2 when generating the water-electrolyzed hydrogen. With this, it becomes possible to calculate the energy E5 consumed by the water electrolyzer 2 when generating the water-electrolyzed hydrogen based on the actually measured power consumption.

(4) The calculation unit 13 further calculates the evaluation value of the energy balance ΔEout(m)/ΔEin(m) based on the difference ΔEin(m) between the standard input energy Ein(0) for the case where the water-electrolyzed hydrogen is not supplied by the hydrogen supply unit 3 and the input energy Ein(m) for the case where the water-electrolyzed hydrogen is supplied by the hydrogen supply unit 3, and the difference ΔEout(m) between the standard recovered energy Eout(0) for the case where the water-electrolyzed hydrogen is not supplied by the hydrogen supply unit 3 and the recovered energy Eout(m) for the case where the water-electrolyzed hydrogen is supplied by the hydrogen supply unit 3. The determination unit 14 determines the supply amount m of the water-electrolyzed hydrogen to be supplied by the hydrogen supply unit 3 based on the evaluation value of the energy balance ΔEout(m)/ΔEin(m) calculated by the calculation unit 13. Specifically, the determination unit 14 determines the supply amount m of the water-electrolyzed hydrogen so that the evaluation value of the energy balance ΔEout(m)/ΔEin(m) becomes "1" or higher. With this, it becomes possible to operate the fuel production system 100 in an operation range where the energy conversion efficiency of the whole system increases by supplying the water-electrolyzed hydrogen.

(5) The water electrolyzer 2 electrolyzes water using renewable power. When using renewable power such as solar power or wind power, the power may be insufficient depending on weather conditions and the like, and the water electrolyzer 2 may not be able to operate at the rated capacity. In such case, the electrolysis efficiency p of the water electrolyzer 2 may decrease and the energy conversion efficiency of the whole fuel production system 100 rather decreases by supplying the water-electrolyzed hydrogen. By monitoring the energy conversion efficiency of the whole fuel production system 100 through the input energy Ein(m) and the recovered energy Eout(m), it becomes possible to properly suppress the energy loss in the fuel production.

Although, in the above, for example, in FIG. 1, the gasifier 4 generates the synthesis gas from the biomass, a synthesis gas generation unit configured to generate synthesis gas containing hydrogen and carbon monoxide from carbon-containing raw material is not limited to the above described configuration. For example, the synthesis gas generation unit may separate and recover carbon dioxide from the factory exhaust gas or the like by DAC (Direct Air Capture) and generate carbon monoxide and water from the recovered carbon dioxide and the water-electrolyzed hydrogen by a reverse equilibrium reaction (reverse shift reaction) of the formula (v).

Although, in the above, for example, in FIG. 1, the fuel production unit 5 produces the methanol fuel, a fuel production unit configured to produce fuel from the synthesis gas is not limited to the above described configuration. For example, the fuel production unit may further synthesize gasoline fuel from methanol by MTG (methanol-to-gasoline) method, or synthesize diesel fuel from the synthesis gas by FT (Fischer-Tropsch) method.

Although, in the above, the water electrolyzer 2 electrolyzes water using the renewable power, a water electrolyzer is not limited to the above described configuration. For example, the water electrolyzer may use power from the commercial power grid instead of renewable power or combine these powers.

Although, in the above, for example, in FIG. 1, all of the water-electrolyzed hydrogen generated by the water electrolyzer 2 is supplied to the gasifier 4, a hydrogen supply unit configured to supply the water-electrolyzed hydrogen generated by the water electrolyzer to the synthesis gas generation unit is not limited to the above described configuration. For example, the hydrogen supply unit may include a hydrogen tank for storing the water-electrolyzed hydrogen, a flow control valve for controlling flow rate of the water-electrolyzed hydrogen supplied to the gasifier, or the like. The operation of the water electrolyzer 2 may be stopped when the electrolysis efficiency p of the water electrolyzer 2 decreases below the predetermined electrolysis efficiency p0 depending on weather conditions and the like.

Although, in the above, for example, in FIG. 3, a specific example of energies has been shown and described as the input energy and the recovered energy of the fuel production system 100, an input energy and a recovered energy are not limited to these energies.

The above embodiment can be combined as desired with one or more of the aforesaid modifications. The modifications can also be combined with one another.

According to the present invention, it becomes possible to suppress the energy loss and the fuel production cost while in the fuel production.

Above, while the present invention has been described with reference to the preferred embodiments thereof, it will be understood, by those skilled in the art, that various changes and modifications may be made thereto without departing from the scope of the appended claims.

The invention claimed is:

1. A fuel production system, comprising:

a synthesis gas generation unit configured to generate synthesis gas containing hydrogen and carbon monoxide from carbon-containing raw material;

a fuel production unit configured to produce fuel from the synthesis gas generated by the synthesis gas generation unit;

a water electrolyzer configured to electrolyze water to generate water-electrolyzed hydrogen;

a hydrogen supply unit configured to supply the water-electrolyzed hydrogen generated by the water electrolyzer to the synthesis gas generation unit; and a controller including an arithmetic unit and a storage unit, wherein the controller is configured to perform:

calculating an input energy based on a first energy possessed by the carbon-containing raw material, a second energy consumed by the water electrolyzer when generating the water-electrolyzed hydrogen, a third energy consumed by the synthesis gas generation unit when generating the synthesis gas, and a fourth energy consumed by the fuel production unit when producing the fuel;

calculating a recovered energy based on a fifth energy possessed by the fuel produced by the fuel production unit; and determining a supply amount of the water-electrolyzed hydrogen to be supplied by the hydrogen supply unit based on the input energy and the recovered energy calculated.

2. The fuel production system according to claim 1, wherein the controller is configured to perform:

calculating the second energy based on a generation amount of the water-electrolyzed hydrogen generated by the water electrolyzer and an electrolysis efficiency of the water electrolyzer.

3. The fuel production system according to claim 1, wherein the controller is configured to perform:

calculating the second energy based on a power consumption consumed by the water electrolyzer when generating the water-electrolyzed hydrogen.

4. The fuel production system according to claim 1, wherein the controller is configured to perform:

calculating an evaluation value of an energy balance based on a difference between a standard input energy for a case where the water-electrolyzed hydrogen is not supplied by the hydrogen supply unit and the input energy for a case where the water-electrolyzed hydrogen is supplied by the hydrogen supply unit, and a difference between a standard recovered energy for the case where the water-electrolyzed hydrogen is not supplied by the hydrogen supply unit and the recovered energy for the case where the water-electrolyzed hydrogen is supplied by the hydrogen supply unit; and determining the supply amount of the water-electrolyzed hydrogen to be supplied by the hydrogen supply unit based on the evaluation value of the energy balance calculated.

5. The fuel production system according to claim 1, wherein the water electrolyzer electrolyzes the water using renewable power.

* * * * *